United States Patent [19]

Krueger

[11] Patent Number: 4,730,917
[45] Date of Patent: Mar. 15, 1988

[54] METHOD AND AN APPARATUS FOR DETERMINING THE REFRACTION

[76] Inventor: Helmut Krueger, Toblerstrasse 76, Zurich, Switzerland

[21] Appl. No.: 901,259

[22] Filed: Aug. 28, 1986

Related U.S. Application Data

[62] Division of Ser. No. 552,053, Oct. 7, 1983, Pat. No. 4,637,700.

[30] Foreign Application Priority Data

Feb. 12, 1982 [DE] Fed. Rep. of Germany ....... 3204876
Feb. 10, 1983 [WO] PCT Int'l Appl. ..................... 002511

[51] Int. Cl.$^4$ .............................................. A61B 3/10
[52] U.S. Cl. ..................................... 351/211; 351/205
[58] Field of Search ................. 351/205, 211, 214, 224

[56] References Cited

U.S. PATENT DOCUMENTS 3,791,719 2/1974 Kratzer et al. ....................... 351/211
4,079,248 3/1978 Lehureau .

FOREIGN PATENT DOCUMENTS 1089561 9/1960 Fed. Rep. of Germany .
1955859 5/1971 Fed. Rep. of Germany .
2836428 5/1980 Fed. Rep. of Germany .

OTHER PUBLICATIONS

Cornsweet et al., Journal of Optical Society of America, Apr., 1970, vol. 60, pp. 549, 550.

Primary Examiner—Bruce Y. Arnold
Assistant Examiner—P. M. Dzierzynski
Attorney, Agent, or Firm—Cushman, Darby & Cushman

[57] ABSTRACT

The invention relates to a method for determining the refraction of the human eye. The retinal image of an object is imaged via a lens system into an object space and into an image plane which is conjugated with respect to the retina. The spacing of the conjugated plane is analyzed to determine the refraction of the human eye. This analysis is carried out by means of a measuring object which is moved along a plane which is defined by rays of the beam of rays which pass through image points of the retinal image of a target object, such that the beam of rays is divided into two complementing partial beams containing an unevenly divided amount of light energy. The unevenly divided light energy is used to determine the distance of said conjugated plane.

23 Claims, 12 Drawing Figures

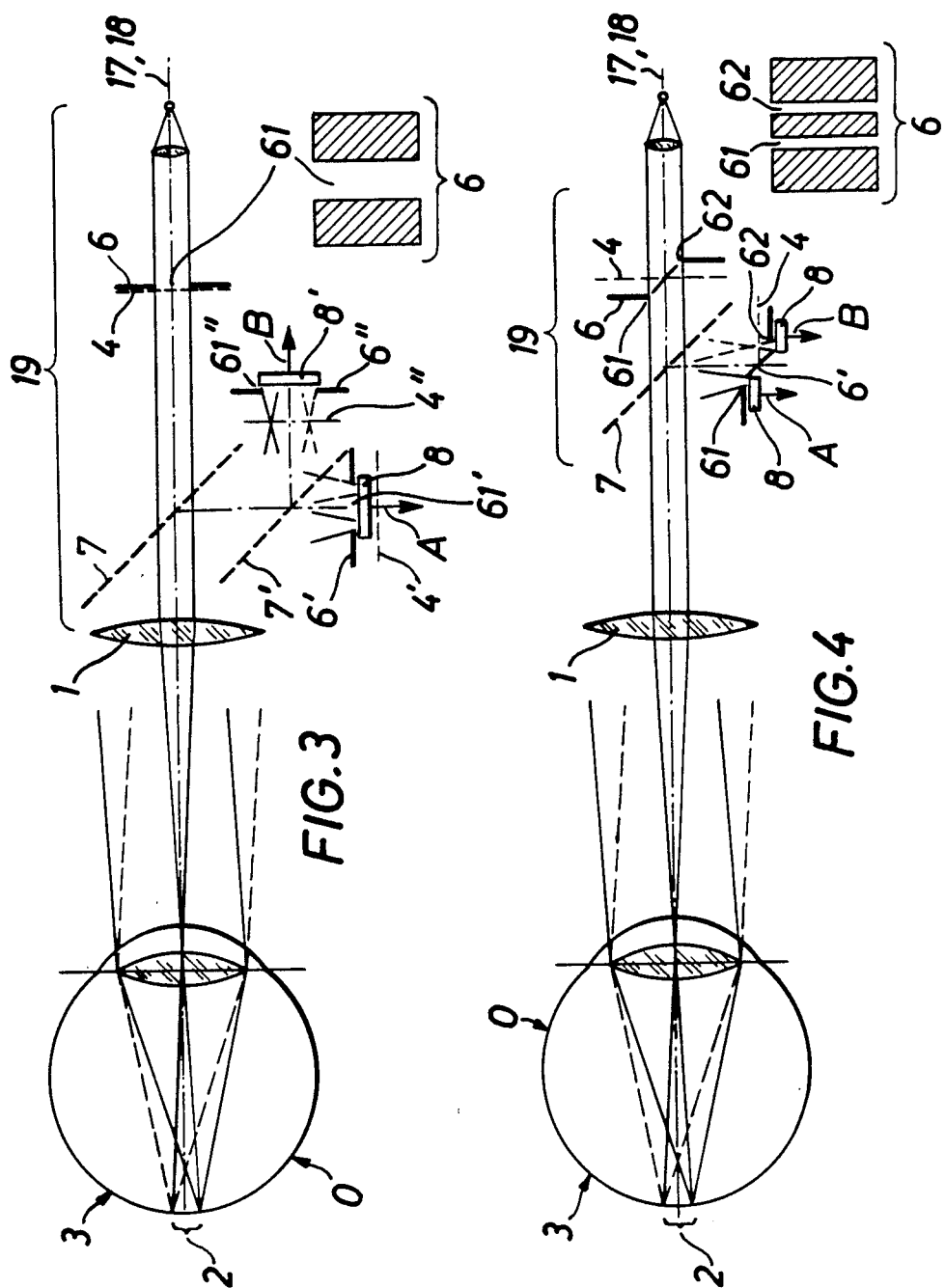

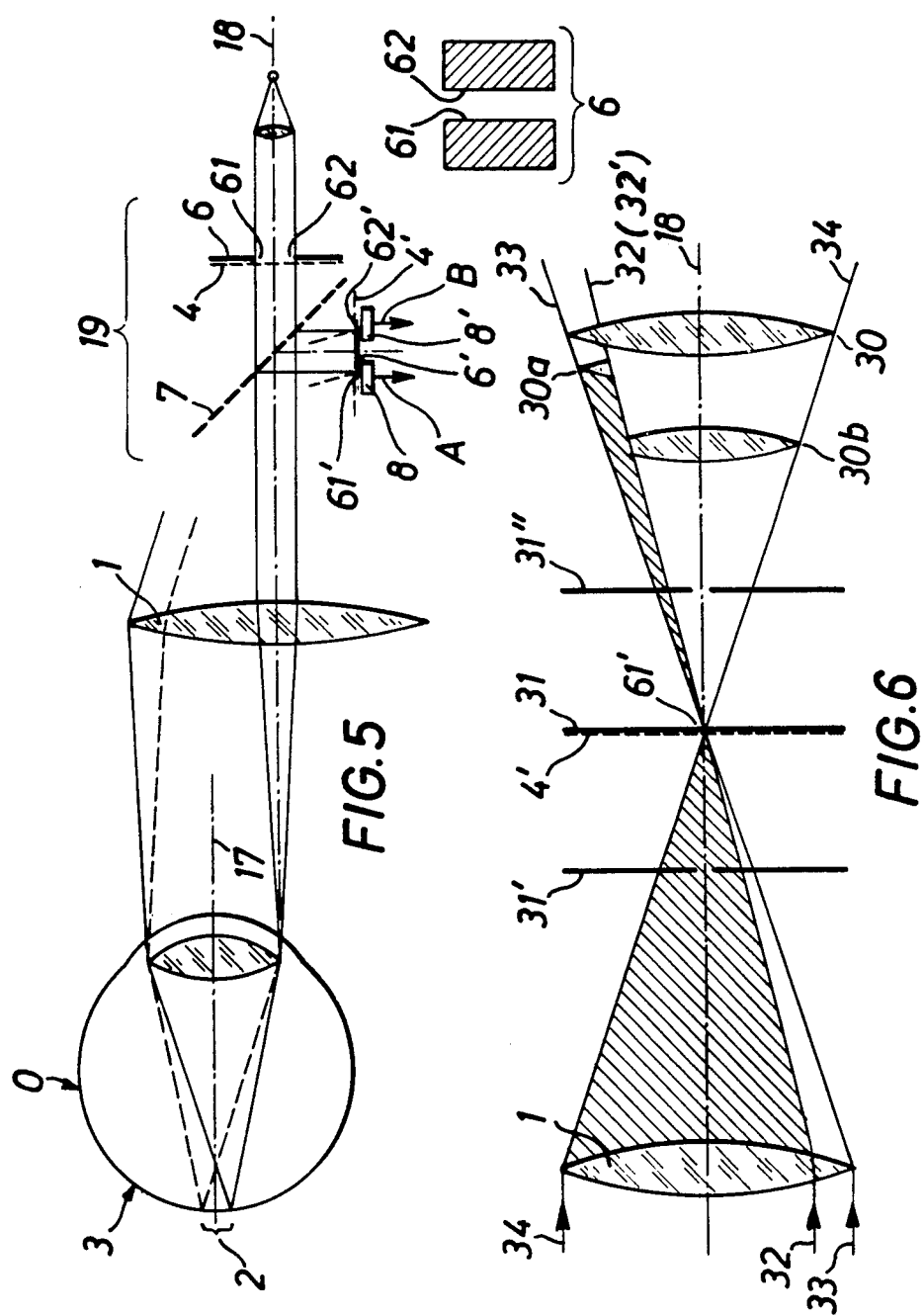

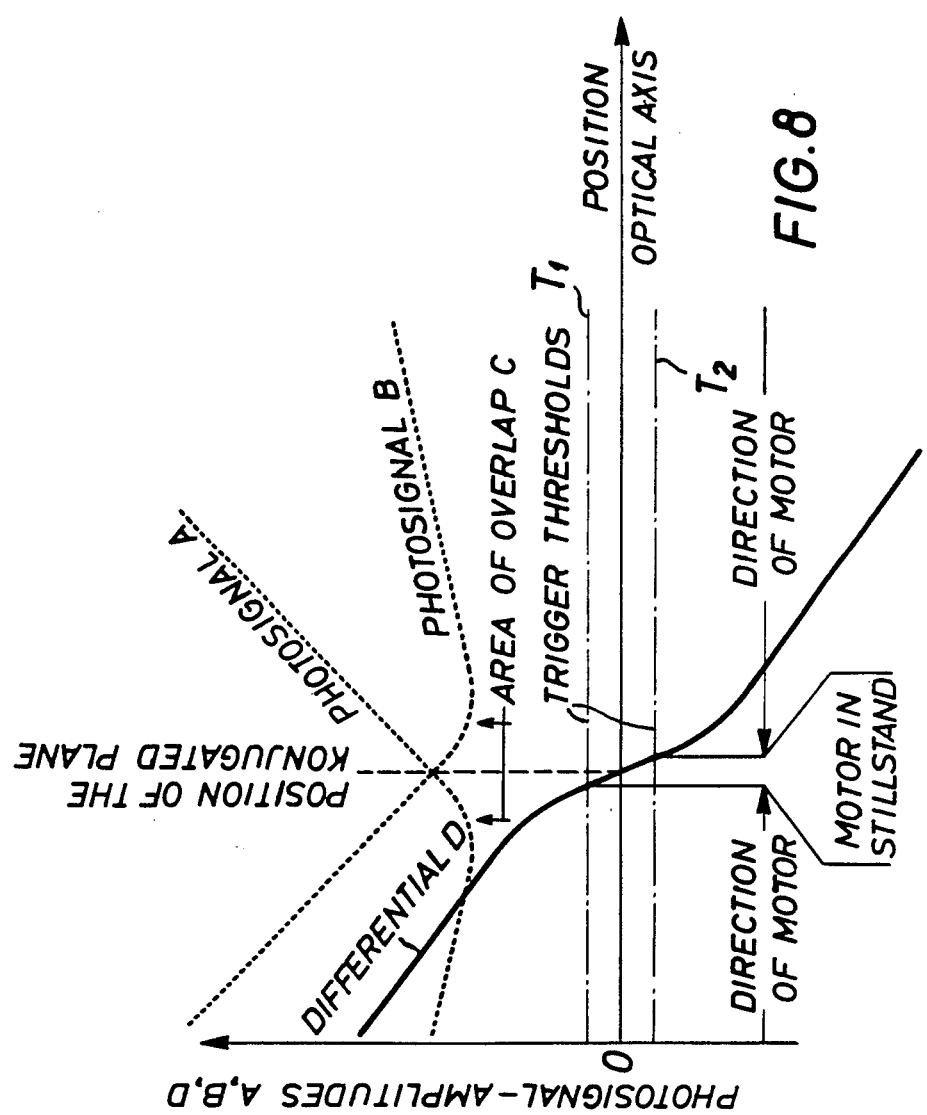

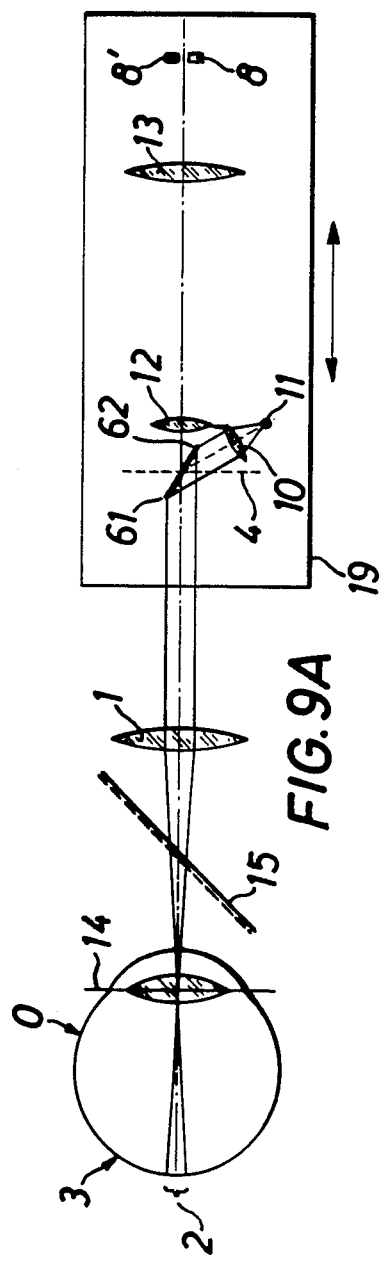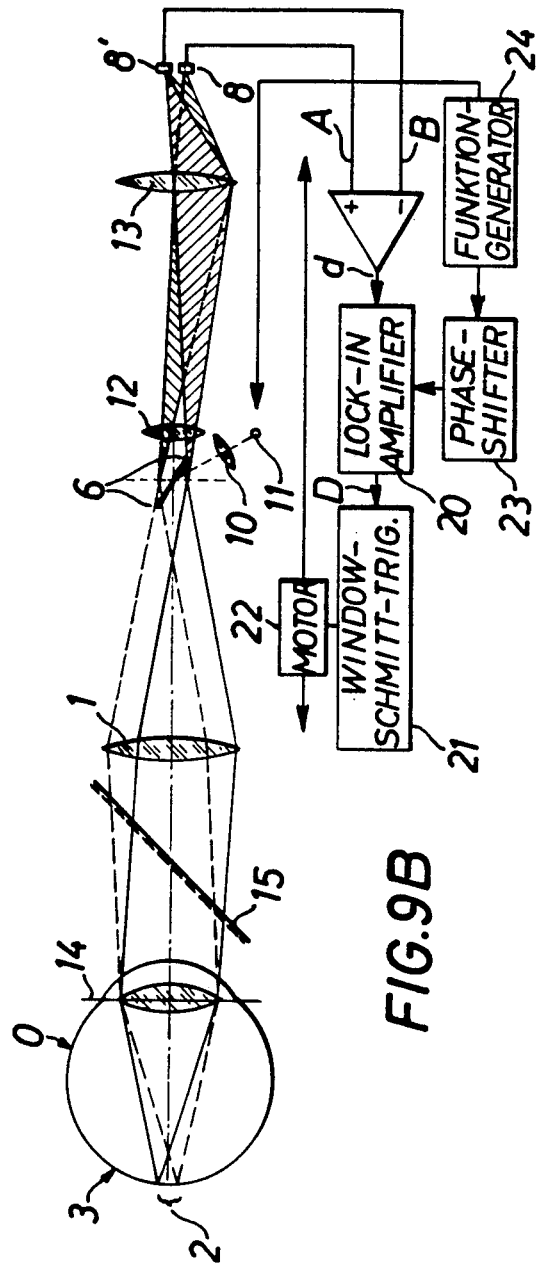
FIG.9A
FIG.9B

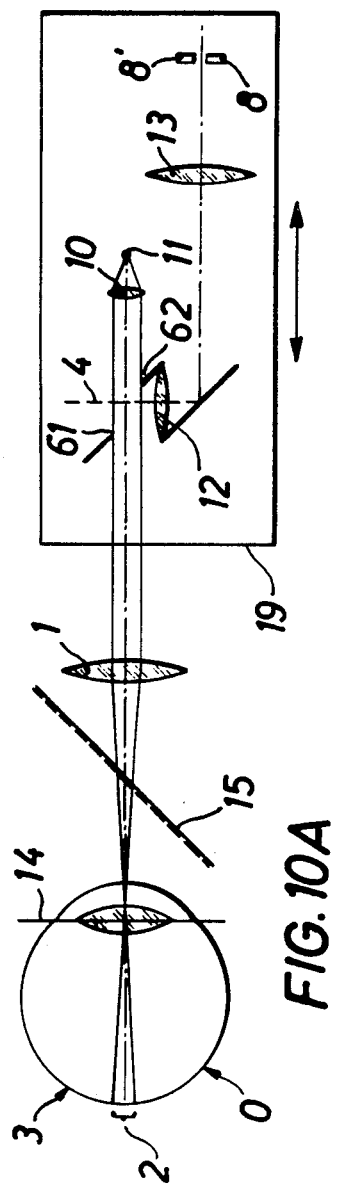
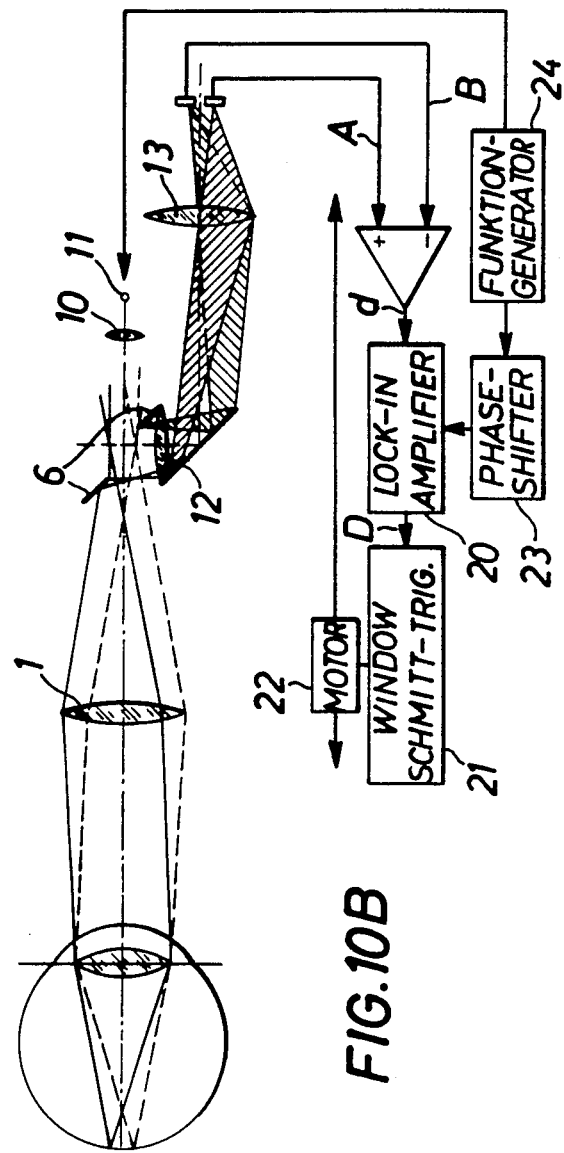
FIG. 10A
FIG. 10B

METHOD AND AN APPARATUS FOR DETERMINING THE REFRACTION

The invention relates to a method and an apparatus for determining the refraction of the human eye, i.e., in short, the status of refraction of the human eye. The invention relates specifically to a method for determining the status of refraction depending on the time. In accordance with the invention an object in the object space is imaged by means of an optometer lense system, in short an optometer lense, onto the retina of the eye; the retinal image of said object, in turn, is imaged back via said optometer lense into the object space into a certain image plane, said image plane being conjugated to the retina and being defined by the status of refraction of the eye and the refracting power of the optometer lense; the distance of said image plane from said optometer lense being representative of the status of refraction, and wherein according to the invention for determining said distance the beam of rays coming from said retinal image is analysed at locations having different distances with respect to said image plane.

Automatic methods for determining the refraction are known (see FIG. 1). According to said known methods the image plane conjugated with respect to the retina of the tested eye is detected. The methods known from German Auslegeschrifts Nos. 29 37 891, 31 10 576, 31 02 450 provide for the imaging of an object, which may have the form of a grating, a point, or a slit, by means of an optometer lense system onto the retina.

The retinal image is reflected back (as a reflected image) into the object space by means of the optometer lense and a beam split mirror (beam splitter). Said reflected image is analysed in the object space by means of another target object. For the purposes of said analysis the luminous flux which is transmitted by said target object is determined by a photo sensitive element. It is therefore necessary that both objects correspond to each other as far as shape and dimension are concerned. So as to detect the conjugated image plane, the two objects are moved together with the beam splitter along the optical axis, or, according to a different method, the refracting power of the optometer lense system is varied. As soon as the position of the conjugated plane is found, a maximum, or depending on the kind of arrangement used, a minimum, of the luminous flux is measured behind the target object by means of the photo sensitive element. The refracting power of the eye is not supposed to vary during said movement. With such a method the variation of the refracting power of the eye depending on time can not be determined without difficulties.

German Auslegeschrift No. 22 62 886 provides for an improvement by periodically moving the object system with high frequency for only a small distance along the optical axis. The result is a periodic change of the photo signal synchronous to said periodic movement. From the phase shift between the movement of the object system and the photo signal an electrical photo signal may be derived for a sufficiently high oscillation frequency, a photo signal which indicates into which direction the object system has to be moved so as to have the conjugated plane being arranged in the center between the points of reversal of the periodic movement. This method has the disadvantage that high mechanical oscillatory frequencies are required, i.e. high values for the acceleration are necessary. Moreover, the determination of the phase is difficult because of the low signal/noise-ratio of the photo signal.

The method of German Auslegeschrift No. 26 54 608 provides for a certain improvement with regard to the mechanical oscillations. Said known method replaces the continuous oscillation by a measurement only at two locations. However, even with this method the signal necessary for controlling the movement of the object system along the optical axis has to be derived indirectly from the phase relation between the physical position and the photo signal.

Another principal method for automatically determining the refraction, is the method of skiascopy, described below.

It is an object of the present invention to avoid the disadvantages of the prior art.

A specific object of the invention is to provide a method and an apparatus for determining the refraction such that a photo signal having a low S/N-ratio is provided, a signal which allows fast determination of the conjugated plane in an easy and precise manner.

The above objects of the invention are solved by characterizing portions of claims 1, 2 and 3. Preferred embodiments of the invention are disclosed in the other claims.

Additional advantages and essential features of the invention may be gathered from the following description of embodiments of the invention; in the drawing:

FIG. 3 is a first embodiment of the invention;

FIG. 4 is a second embodiment of the invention;

FIG. 5 is a third embodiment of the invention;

FIG. 6 is a representation of the principle used for determining the conjugated plane in accordance with the method disclosed in FIG. 5;

FIG. 8 shows the wave form of the photo signals obtained in an experiment when the movable object system is moved in accordance with the method disclosed in FIG. 7;

FIGS. 9a, 9b disclose a fifth and particularly preferred embodiment of the invention;

FIGS. 10a, 10b disclose a modification of the embodiment of FIGS. 9a, 9b.

Figure 1:
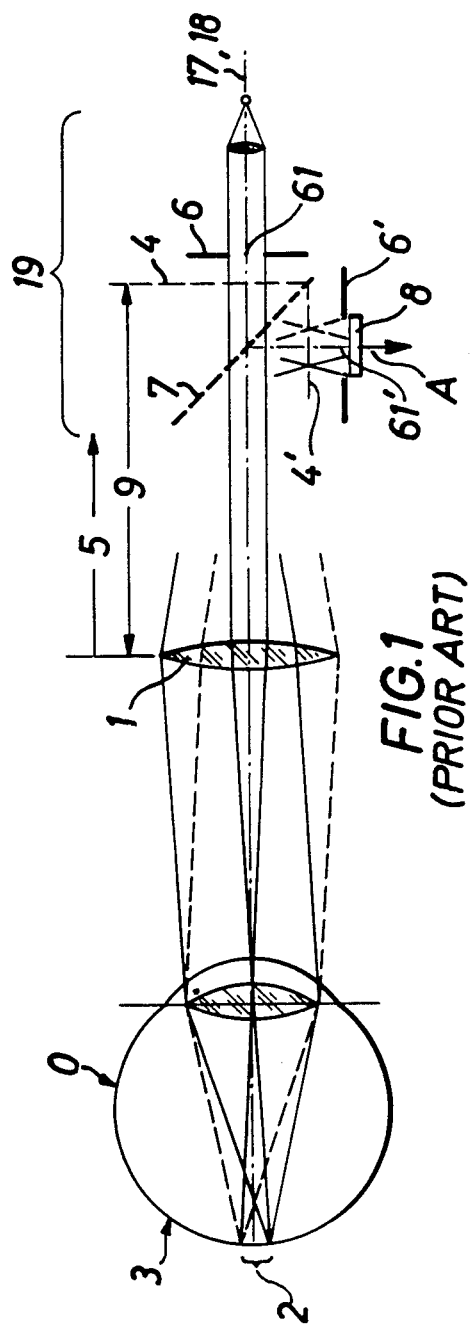
FIG. 1 is a representation of a prior art method for measuring the refraction.

FIG. 1 discloses, as already mentioned, a prior art method for determining the refraction. According to said method an image plane 4 and 4', respectively, an image plane which is conjugated with respect to the retina 3 of an eye O and having a distance 9 from the optometer lense system 1 is detected. Said distance 9 is representative for the status of refraction of the eye O. To this end, an object 6 is imaged onto the retina 3, said object 6 may be in the form of a grating, a point or a slit. An image of the retinal image 2 is reflected back into an object space 5 by means of the optometer lense system 1 (optometer lense 1) and a beam splitter 7; said reflected image is analysed by means of a target object 6' located in said object space. For that purpose the luminous flux which passes the target object 6' is measured.

Figure 2:
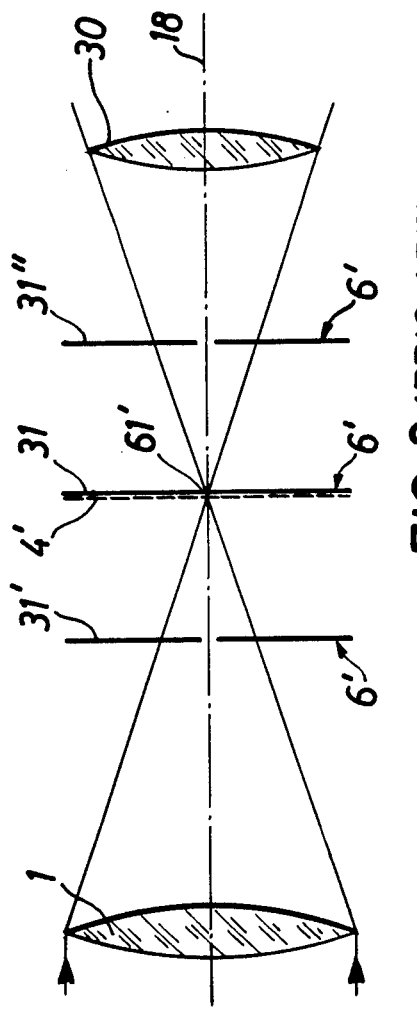
FIG. 2 is a representation of the basic principle used in the measurement method shown in FIG. 1 when detecting the conjugated plane.

For this purpose both objects 6, 6' do have to correspond to each other as far as form and dimension is concerned. So as to detect the conjugated image plane 4 and 4', respectively, the object system 19 comprising the two objects 6, 6' and the beam splitter 7 is moved along the optical axis 18. It would also be possible to have the beam splitter maintain its position. Another possibility would be to change the refracting power of the optometer lense system 1. FIG. 2 explains this situation. In said fig. the imaging beam of rays for one image point 61' (61 in FIG. 1 of the image of a point of the retinal image 2 is marked in the conjugated plane 4' (4). As soon as the target object 6' (which is here for reasons of simplification a pin hole stop) is in front of the conjugated plane 4', e.g. in position 31', a portion of the beam of rays 30 is removed from the target object 6', a portion which corresponds to the amount of defocussing; said portion increases with increasing distance of the target object 6' from the conjugated plane 4'. The same is similarly true for all positions 31" of the target object 6' behind the conjugated plane 4'. Only if the target object 6' is in the conjugated plane 4' (see 31 in FIG. 2) the entire light engergy contained in the beam of rays 30 can pass through said target object 6' in an ideal situation. In such a situation a maximum, or in other embodiments a minimum, of the light flux A delivered from the photo element 8 in FIG. 1 is measured behind the target object 6', said maximum (or minimum) being an indication for the position of the conjugated plane 4' and 4, respectively. The refracting power of the eye O is not supposed to change during the movement along the optical axis 18. With such a method the change of the refracting power of the eye depending on time can not be determined without problems. Reference numeral 17 refers in FIG. 1 to the optical axis of the eye.

In the following figures similar reference numerals, as were used in FIGS. 1 and 2, will be used for similar elements, unless otherwise stated.

FIG. 3 discloses an improvement of the invention relating to the electrical evaluation of the photo signal. In accordance with this improvement measurements are carried out simultaneously before and behind the conjugated plane 4. For this purpose one target object 6' is arranged before the conjugated plane 4', and a second target object 6" is arranged with a fixed distance with respect to 6' behind the conjugated plane 4". This arrangement may be realized for instance by providing another beam splitter 7'. Behind each target object 6', 6" each one photo element 8, 8' is located. If the object system 19 is moved along the optical axis 18 (see FIG. 2) the light flux of the imaging beams of rays 30 (path of beams of measurement), which is transmitted in accordance with FIG. 2 by the target objects 6' and 6", respectively, will steadily decrease with increasing distance from the appropriate conjugated planes 4' and 4". Inasmuch as the two target objects 6' and 6" are moved together maintaining a fixed distance from each other, both said target objects 6' and 6" cannot both be located at the same time in the conjugated plane. The photo signals A and B will consequently reach their maximum for different positions of the object system. The photo element which belongs to the target object which happens to be closer to the conjugated plane will provide the larger photo signal. Only in the case where the two target objects 6', 6" have the same distance from the appropriate conjugated plane 4', 4", i.e. in a situation where the image of the retinal image on the two target objects 6', 6" is equally defocussed and the conjugated plane is arranged between said two objects, then the photo signals A and B are of the same size. In all other cases the difference A−B provides a photo signal for a controlled movement of the object system 19, comprising the elements 7, 7', 6, 6' 6"; 8, 8' in the direction towards the symmetrical position with respect to the planes 4, 4', 4".

In addition to the image point 61' of FIGS. 1 and 2, already explained, another image point 61" is shown. The information concerning the direction of movement is now no longer contained in a phase, but advantageously directly in the amplitude of the photo signals A and B. However, the gain with respect to the S/N-ratio can not be fully utilized, because the additional beam splitter 7' is necessary.

This disadvantage may be overcome (FIG. 4) if the object 6 and the target object 6' are provided with an extension in the direction of the optical axis 18 such that two parallel partial objects 61, 62 and 61' and 62', respectively, are present. If now, as is examplified in FIG. 4, behind each partial object 61' and 62' of the target object 6' a photo element 8, 8' is positioned, a photo element which measures the light flux in the form of photo signals A and B passing through the partial objects 61', 62', it is again possible to find in a determined manner the conjugated plane 4, 4' by means of the clearly directed differential signal (A−B)-similar to the embodiment of FIG. 3-by moving the object system 19 along the optical axis 18. The conjugated plane will be reached when both photo elements 8, 8' provide equal photo signals A and B. Even though in this manner the photo signal is improved, the S/N-ratio is still not favorable for a continuous registration of the condition of refraction.

A completely different method for automatically determining the refraction is the so-called cutting edge method (skiascopy); see for instance German Auslegeschrifts Nos. 2315135, 2951897 and 3020804 which relate to the automatic refractometry. In accordance with this method it is not the sharpness of an image which is checked, but, in the most general sense, the width of a beam of rays is determined, a width which has to be minimal in the conjugated plane. In accordance with such methods, the width of the imaging beam of rays is determined timewise successively at different distances with respect to an optometer lense perpendicular to the optical axis; starting from the differential signal a phase depending value is calculated, a value by means of which a position with the smallest or the same diameter of beam is located. This position is reached when the conjugated plane is arranged in the middle between the two positions of measurement.

The embodiment shown in FIG. 5, in a certain sense, makes use of the skiascopic method. In contrast to the method of the prior art, however, the cutting edges are not moved perpendicular to the direction of rays, but they are moved in the direction of the imaging rays (imaging path of rays). In the explanatory FIG. 6 the imaging beam of rays 30 of one image point of the image of a point of the retinal image 2 in the conjugated plane 4' of FIG. 2 is split by means of a plane 32', a plane which is defined by the imaging beams 32 extending through the image point 61', into two partial beams of rays 30a (hatched) and 30b, respectively, which are above and below said plane 32'. In the two dimensional representation the plane 32' coincides with the beam 32. As is shown in FIG. 6 the beam of rays 30a (30b) has a different light flux before and after the image plane. The closer the plane 32' and the ray 32, respectively, come to the marginal ray 33 and 34, respectively, of the beam of rays 30, the larger is said difference. The change of the light flux of at least one of said partial beams of rays 30a and 30b, respectively, at the location of the conjugated plane 4' is used for finding the conjugated plane 4'. For this purpose the flux of light of at least one of said partial beams of rays 30a, 30b has to be measured along the beam 32, as is shown for example by positions 31' and 31". It is possible to arrange for that purpose, as is shown for the embodiment of FIG. 5, the optical axis 17 of the eye in a parallel offset manner with respect to the axis 18 of the apparatus. At least at one bright/dark transition 61' and a dark/bright transition 62' the flux of light, respectively, which can pass the target object 6' is measured by means of two photo elements 8, 8' in the form of photo signals A and B. An improvement of the electrical S/N-ratios is here obtained because the measurement is carried out not timewise successively, but simultaneously with the consequence that the information is not contained in the phase but in the amplitude of the photo signals A and B. Measurements of the differential signal A—B of the photo elements 8, 8' when moving the object system 19 along the optical axis 18 result in a differential signal which can be well processed so as to find the conjugated plane 4 and 4', respectively. However, the local change of the differential signal, i.e. the sensitivity, is small in the neighborhood of the conjugated plane.

Figure 7:
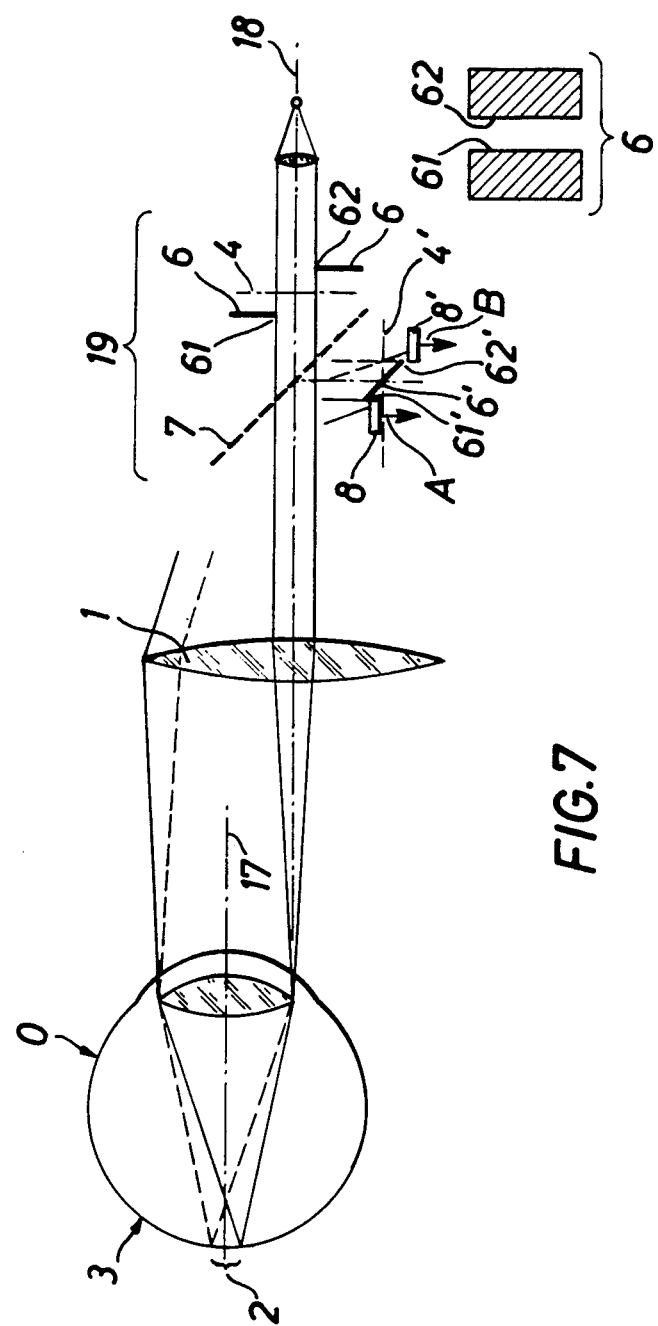
FIG. 7 is a forth and particularly preferred embodiment of the invention.

An additional improvement may be obtained when using the method of the evaluation of sharpness in accordance with FIG. 4 together with the last mentioned method disclosed in FIG. 5; see FIG. 7. By providing a parallel movement of the optical axes 17 and 18 the conditions of FIG. 5 are realized, and by providing the oblique position of object 6 the conditions of FIG. 4 are simultaneously realized. FIG. 8 shows the appropriate form of the photo signals A and B of the two photo elements 8, 8'. The photo element 8 supplies primarily a photo signal A if the appropriate edge 61' of the target object is in front of the conjugated plane 4', and, in contrast thereto, the photo element 8' supplies a photo signal B if it is located behind the conjugated plane 4'. The region of overlap C (see FIG. 8) of the two photo signals, which causes a steeper zero-crossing of the differential D of the two photo signals A and B, is caused by the simultaneous realisation of the additional criteria of sharpness in accordance with FIG. 4.

An additional improvement of the S/N-ratio can be obtained for the method of FIG. 4 as well as for the method of FIGS. 3, 4 and 5 if the beam splitter 7 is deleted and the object 6 itself is provided in the form of a mirror, as is shown for the two embodiments (FIGS. 9 and 10) discussed below; object 6 and target object 6' are reduced to a single object. This solves all problems of adjustment regarding the object 6 and the target object 6', adjustments which otherwise occur due to the high requirements relating to the geometric similarity and the correct optical positioning of the objects 6 and 6'.

Each of the FIGS. 9 and 10 disclose particularly preferred embodiments of the invention, embodiments for which an improvement of the S/N-ratio is possible and which allow the automatic measurement of the status of refraction and the continuous documentation by means of printer and/or plotter, a measurement which is carried out by means of light reflected by the retina while at the same time the energetic stress of the eye is reduced. The two embodiments differ from each other in so far, as the imaging system of FIGS. 9a, 10a and the measuring system of FIGS. 9b, 10b are exchanged. Consequently, the description can be restricted to a description of FIG. 9, and said description can be applied also to FIG. 10.

The optical arrangement of the method comprises an imaging system (in FIGS. 9a and 10a: 1, 6, 61, 62, 10, 11) and a measurement system (in FIGS. 9b, 10b: 1, 6, 61, 62, 12, 13, 8, 8') which is separately depicted for reasons of clarity; said systems are the same with respect to the two essential elements, i.e. optometer lense 1 and object 6. For reasons of simplification the parallel offset arrangement of the optical axes 17 and 18, as shown in FIG. 5, was deleted. It is important that in the imaging system as well as in the measurement system the same object is used. For carrying out the measurement only the optometer lense maintains a fixed distance with respect to the eye, while the other elements 19, having a frame around them, are moved in common in the direction of the optical axis, or, alternatively, the image side focal length of the optometer lense is varied. So as to determine the refraction of the eye in different principal sections, the arrangement may be rotated about the optical axis of the system, or, when the method of FIG. 7 is realized, the rotation may be provided about an axis parallel thereto. The frontal principal plane 14 of the eye coincides with the frontal focal plane of the optometer lense 1.

The imaging path of rays (FIG. 9a): In the refractometer according to the invention an object 6 is obliquely arranged with respect to the optical axis 18 having two partial objects in the form of parallel bright/dark 61 and dark/bright edges 62, edges which are illuminated from the front by means of a high frequency modulated light having a low aperture. The illumination may be carried out by means of a light emitting diode 11 which for example emits light having a wave length of 820 nm and is located in the focal point of a condensor 10. The use of light having a low aperture provides by means of the optometer lense 1 a small artificial entrance pupil of the imaging beam of rays in the frontal principal plane 14 of the eye. The consequence is that also the aperture in the eye is small and the object 6 has, as seen from the subject the form of a dark red illuminated slit, which, in praxis is sharply seen over a wide range of distances of vision. The mechanism of accomodation is, consequently, not disturbed by the imaging system. So as to minimize objectionable reflexes the optometer lense 1 may be inclined with respect to the optical axis 18, or else for the imaging of the object onto the retina polarized light might be used which is depolarized on the retina, said light will maintain to a large degree its direction of polarisation when being reflected at reflecting surfaces. Said reflections may be separated from the reflected light of the retina by means of a crossed analyser arranged in the beam of measurement.

Beam of measurement (FIG. 9b): The retinal image 2 of the object having the parallel edges 61, 62 forming partial objects is reimaged onto the object 6 which creates the retinal image 2, said reimaging being effected by means of the light reflected by the retina 3 via the optical arrangement of the imaging system and the optometer lense 1. At the edges a portion of the light will not return to the path of the imaging beam, said portion of the light corresponds to the defocussing and for optical axes being parallel offset, to the width of the beam of rays; said portion of the light will, instead, pass into the path of the measurement beam 12, 13, 8, 8' (hatched beam of rays). For the detection of the rejected defocussed portion of the high frequency modulated energy reflected at the retina 3 each of said two object edges (partial objects 61,62) is imaged by means of a lense 13 via a field lense 12 onto one of said two photo elements 8, 8'. Inasmuch as the frontal principal plane 14 of the eye (approximately the plane of the pupil) falls together with the focal plane of the optometer lense 1, and because the lense 13 is arranged in the backward focal plane of the lense 12, the two lenses 1 and 12 form a telecentric system, a system which independently from the position of the movable object arrangement 19 images the frontal principal plane 14 of the eye onto the lense 13. As a consequence thereof it is possible to possibly remove in front of lense 13 undesired reflexes of the imaging system in the frontal eye media. This will not be necessary if optical eye axis and the axis of the apparatus are parallel offset. In case that polarized light is used it is possible to arrange between object 6 and photo elements 8, 8' a crossed analyser which will filter out the light occurring at the lense surfaces having mirror characteristics.

Determination of the conjugated image plane: In case that for a fixed distance of vision of the eye (accomodation) the movable apparatus 19, shown in the drawing within an enclosure, is moved along the optical axis 18, each of the proportions of the reflected light separated at each edge (partial objects 61,62) of the object 6, proportions which lead to the differential signal D of the photo elements 8, 8', will first decrease starting from the optometer lense 1 with increasing distance from said optometer lense 1 corresponding to the position of plane 4 conjugated with respect to retina 3, the zero crossing being in plane 4 and thereupon another decrease is following (see in FIG. 8 the difference D). The differential signal D will exactly pass through the value zero when the two object edges 61, 62 are symmetrically equally distantly located from the conjugated plane 4. Therefore, a zero method being relatively undisturbable is being provided. It is the object of the method to position the movable arrangement 19 such that the two object locations 61 and 62 are symmetrically located with respect to plane 4. For this purpose the movable part has to be positioned with respect to the lense 1 in a close loop control circuit such that the differential signal becomes zero (see FIG. 8).

The electronic photo signal processing (FIGS. 9b, 10b): So as to improve the S/N-ratio and for filtering out room light, the light of measurement (for example the light of a LED) is high frequency modulated. The differential signal d of the photo elements 8, 8' is amplified in a phase locked manner and amplified (lock-in amplifier 20). The differential signal D thus amplified is fed into a Window-Schmitt-trigger 21 having two trigger thresholds T1 and T2 (see FIG. 8) which can be symmetrically adjusted with respect to zero volt. Said trigger supplies at its output signals for no movement, movements towards the left and movements towards the right of the motor drive 22 of the movable apparatus 19. In case that the differential signal D is between the two trigger thresholds T1 and T2, the position remains unchanged. In case that the two thresholds T1, T2 are exceeded or underceeded, the movable apparatus 19 is moved along the optical axis 18 so long until the differential signal D is between said two thresholds T1, T2. The light source 11 is controlled by means of a function generator 24 which simultaneously controls via a phase shifter 23 the lock-in amplifier 20. The distance 5 (see FIG. 7) from the optometer lense 1 is the measurement value of the refraction value of the eye, a value which is obtained for the sharp fixation of an object of vision in a predetermined distance from the eye. The determination of this distance 5 can for instance be determined by using a step motor considering the number of steps, or by means of a coupled potentiometer.

Visible target: For the determination of the condition of refraction visible targets have to be offered to the subject; said visible targets have to be offered to the subject; said visible targets are necessary for the fixation of the direction of vision and for the adjustment of distance of the eye for the aim of measurement in question (i.e. refraction, accomodation); said visible targets are adapted to stimulate the accomodation. Said targets are projected between eye O and optometer lense 1 by means of an achromatic or, even better, a dichroitic beam splitter mirror 15.

Recording of measured values: The values of refraction are supplied at the output of the electronic means as analog or digital voltage values. Said values are, by means of ordinary printers, recorded, printed and further processed. By rotating the arrangement 1, 19 about the optical axis of the eye values of refraction for the different main sections may be obtained when linear objects 6 (slit or grid) are used, values from which the astigmatism with its direction of axis may be derived. This can be done in the form of ordinary characteristics which are numerically printed out, or, because of the good time resolution of the method of the invention the output may be provided in graphic form, a form which allows an interpretation with respect to the regularity of an astigmatism in addition to the information given by the characteristics. In view of the good time resolution of the method of the invention the adjustment of the eye to distance depending on the time can be recorded parallel to the dependence on the distance of the visual object (refraction - time - characteristics) and it is possible to determine aberrations of the system of accomodation prior to their showing with measurements of static equilibrium adjustments without taking into consideration the time.

I claim:

1. A method for determining the time dependent refraction of the human eye comprising the steps of:
   (a) imaging a target object having an extension in depth in the direction of the optical axis in an object space onto the retina of the eye with an optometer lense system such that the retinal image of said object is re-imaged via said lense system into the object space and into an image plane which is conjugated with respect to the retina and depends on the refraction of the eye and the index of refraction of the lense system, the distance of said conjugated image plane from said lense system being a measure of refraction,
   (b) separating the beam of rays from the target object from the beam of rays from the retinal image by means of said target object comprising at least two parial portions, said partial portions being edges of the target object and extending parallel to each other, and
   (c) simultaneously analyzing the beam of rays from the retinal image at at least two different distances from the conjugated image plane by means of said target object.

2. The method of claim 1 wherein said partial portions are illuminated by means of a light source and a condensor in a reflecting manner.

3. The method of claim 1 wherein said partial portions are illuminated by means of a light source and a condensor in a transmitting manner.

4. The method of claim 1 wherein said object comprises a mirror.

5. The method of claim 1 wherein the beam of rays from the retinal image is analyzed so as to determine said distance of the conjugated plane by means of a measuring object, wherein said measuring object is guided along at least one plane through said beam of rays from said retinal image, said plane being defined by rays of the beam of rays which pass through image points of the retinal image of the target object, and divides the beam of rays into two complementing partial beams such that the light energy of the beam of rays is unevenly divided between said complementing partial beams, causing unevenly divided light energy in said partial beams, said unevenly divided light energy being used to determine said distance of said conjugated plane.

6. The method of claim 5 wherein the target object and the measuring object each comprise two edges, and wherein further the measuring object is guided with each edge along a plane such that partial beams having oppositely distributed light energy are measured.

7. The method of claim 5 wherein the measuring object is moved along the optical axis until the difference between the light energies of the partial bundles having oppositely distributed light energy is zero.

8. The method of claim 5 wherein the measuring object comprises at least one bright/dark and dark/bright edge which are used separately for carrying out the measurement.

9. A method for determining the time-dependent refraction of the human eye comprising the steps of:
(a) imaging a target object in an object space onto the retina of an eye with an optometer lense system such that the retinal image of said object is re-imaged via said lense system into the object space and into an image plane which is conjugated with respect to the retina and depends on the refraction of the eye and the index of refraction of the lense system, the distance of said conjugated image plane from said lense system being a measure of refraction,
(b) separating the beam of rays from the target object from the beam of rays from the retinal image, and
(c) analyzing the beam of rays from the retinal image so as to determine said distance of the conjugated plane by means of a measuring object wherein said measuring object is guided along at least one plane through said beam of rays from said retinal image, said plane being defined by rays of the beam of rays which pass through image points of the retinal image of the target object, and divides the beam of rays into two complementing partial beams such that the light energy of the beam of rays is unevenly divided between said two complementing partial beams, causing unevenly divided light energy in said partial beams, said unevenly divided light energy being used to determine said distance of said conjugated plane.

10. The method of claim 9 wherein said plane is placed such that the partial beam located on one side of said plane contains a negligibly small portion of said light energy.

11. The method of claim 9 wherein the optical axis of the beam of rays from the target object and of the axis of the eye are parallel and offset to each other.

12. The method of claim 9 wherein the edges of the target object and of the measuring object are offset in longitudinal direction with respect to the appropriate optical axes.

13. The method of claim 8 wherein said measuring object comprises at least one mirror.

14. The method of claim 8 wherein the target object and measuring object are the same.

15. The method of claim 8 wherein the measuring object comprises light sensitive elements.

16. The method of claim 9 wherein the edges of said measuring object are parallel to each other.

17. The method of claim 9 wherein the measuring object cooperates with light sensitive elements, said light sensitive elements providing output signals A, B by means of which a differential signal (A−B) is formed.

18. The method of claim 17 wherein the differential signal A−B is a control signal for automatically determining the image plane.

19. The method of claim 18 wherein the differential signal A−B is amplified free of noise by means of a lock-in amplifier.

20. The method of claim 9 wherein the system for carrying out the measurement is mechanically or optically rotated about the optical axis of said measuring system or about an axis parallel thereto.

21. The method of claim 9 wherein the imaging of the object onto the retina occurs by means of high-frequency modulated light.

22. The method of claim 9 wherein for the imaging of the object infra-red light is used.

23. The method of claim 9 wherein the aperture of the imaging system is selected to be small.

* * * * *